United States Patent [19]

Ojima et al.

[11] Patent Number: 4,497,964
[45] Date of Patent: Feb. 5, 1985

[54] PROCESS FOR PRODUCTION OF N-ACYL-α-AMINO ACIDS

[75] Inventors: Iwao Ojima; Kenji Hirai, both of Sagamihara, Japan

[73] Assignee: Sagami Chemical Research Center, Tokyo, Japan

[21] Appl. No.: 441,853

[22] Filed: Nov. 15, 1982

[30] Foreign Application Priority Data

Nov. 17, 1981 [JP]  Japan ................................ 56-183146

[51] Int. Cl.³ ............................................. C07C 51/12
[52] U.S. Cl. ................................... 562/406; 260/404; 546/268; 546/281; 546/284; 546/323; 546/335; 548/492; 548/494; 548/495; 548/517; 548/527; 548/537; 549/60; 549/69; 549/72; 549/76; 549/487; 549/493; 562/497; 562/517
[58] Field of Search ................. 562/406, 497, 517, 520; 260/404; 546/281, 284, 268, 323, 335; 548/537, 527, 495, 492, 494, 507, 517; 549/60, 69, 72, 70, 76, 487, 493

[56] References Cited

U.S. PATENT DOCUMENTS 3,766,266 10/1973 Wakamatsu ......................... 562/406
4,264,515 4/1981 Stern ................................. 260/404

FOREIGN PATENT DOCUMENTS 2364039 7/1974 Fed. Rep. of Germany ...... 562/406
48-17259 5/1973 Japan.

OTHER PUBLICATIONS

Hawley, "The Condensed Chemical Dictionary," 8th Ed., pp. 28, 80 and 657 (1971).

Primary Examiner—Michael L. Shippen

Attorney, Agent, or Firm—Wenderoth, Lind & Ponack

[57] ABSTRACT

A process for the production of an N-acyl-α-amino acid represented by the general formula

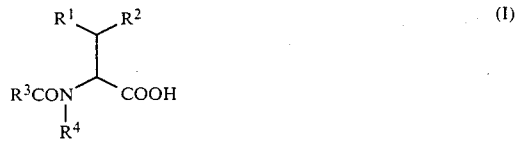

wherein $R^1$, $R^2$, $R^3$ and $R^4$, independently from each other, represent a hydrogen atom, an alkyl or cycloalkyl group which may be substituted, or an aryl or heteroaromatic group selected from the group consisting of furyl, pyrrolyl, pyridinyl, thienyl and indolyl which may be substituted, which comprises reacting an oxirane represented by the general formula

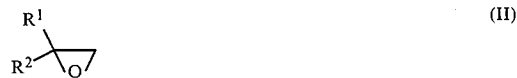

wherein $R^1$ and $R^2$ are as defined above, an amide compound represented by the general formula

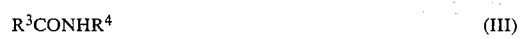

wherein $R^3$ and $R^4$ are as defined above, and carbon monoxide in the presence of hydrogen, a cobalt-containing catalyst, and a promoter composed of a compound containing a metal selected from Groups I, II, III and IV of the periodic table.

15 Claims, No Drawings

PROCESS FOR PRODUCTION OF N-ACYL-α-AMINO ACIDS

This invention relates to a process for the production of N-acyl-α-amino acids, and more specifically, to a process for the production of N-acyl-α-amino acids represented by the general formula

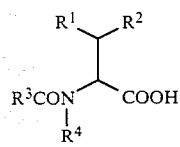 (I)

wherein $R^1$, $R^2$, $R^3$ and $R^4$, independently from each other, represent a hydrogen atom, an alkyl group which may be subsituted, or an aryl group which may be substituted.

Amino acids have heretofore been known to be produced by (1) separation from hydrolyzates of natural proteins, (2) fermentation, or (3) chemical synthesis, depending upon the kinds of the amino acids to be produced. Today, except for certain amino acids, production of amino acids is carried out by a fermentative method or a chemical synthesis method.

Chemical synthesis method for the production of amino acids require optical resolution except for a method which comprises asymmetrically hydrogenating an N-acyldehydroamino acid synthesized by the Erlenmeyer method [for the asymmetric hydrogenation, see V. Caplar, G. Comisso and V. Sunjic, Synthesis, 85 (1981)], and subsequently hydrolyzing the product. The optical resolution of an N-acylamino acid by an acylase is known as a method which is most efficient and has been found to be industrially advantageous by many research workers. Accordingly, if a process for producing an N-acylamino acid with good efficiency is discovered, it will be directly useful for the industrial production of amino acids.

For the industrial production of N-acylamino acids, the so-called Wakamatsu reaction is known which gives N-acylamino acids in one step from aldehydes, amides and carbon monoxide as starting materials using cobalt carbonyl [see Hachiro Wakamatsu, Journal of the Society of Petroleum, 17, 105 (1974)]. Because this method uses aldehydes as starting materials, it cannot avoid competition with the Strecker method, and has not necessarrily acquired an advantageous status in industrial production.

Phenylalanine is a typical example of amino acids which are produced industrially by chemical synthesis method. Phenylalanine is produced by the Strecker method, the Erlenmeyer method [see "Amino Acid Industry —Synthesis and Utilization", a Japanese-language publication edited by Kaneko, Izumi, Chihata, and Ito, published by Kodan Sha, Tokyo Japan, 1973], etc. The Strecker method has the defect that expensive phenyl acetaldehyde is used as a starting material, hydrogen cyanide is used, large amounts of acids and alkalies are required, and the generation of large amounts of waste liquors is inevitable. The Erlenmeyer method which involves using acetylglycine has many reaction steps including condensation, hydrolysis, hydrogenation, etc., and further has the defect that hydrogenation requires Raney nickel which is difficult to handle.

Japanese Patent Publication No. 17259/1973 gives an example (Example 12) in which N-acetylphenylalanine was synthesized from styrene oxide and acetamide as starting materials under the conditions of the Wakamatsu reaction using dicobalt octacarbonyl as a catalyst. The present inventors have traced this Example, but obtained the final product only in such a low yeild as to be unsuitable for industrial production (see Comparative Example given hereinbelow).

The present inventors have assiduosly made investigations in order to overcome the defects of the prior art, and have now found suprisingly that an N-acyl-α-amino acid can be produced in one step by reacting an oxirane, an amide and carbon monoxide in the presence of a catalyst system composed of a cobalt catalyst and a specified promoter.

Thus, according to this invention, there is provide a process for producing an N-acyl-α-amino acid represented by the formula

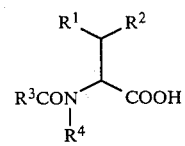 (I)

wherein $R^1$, $R^2$, $R^3$ and $R^4$, independently from each other, represent a hydrogen atom, an alkyl or cycloalkyl group which may be substituted , or an aryl or heteroaromatic group selected from the group consisting of furly, pyrrolyl, pyridinyl, thienyl and idolyl which may be substituted, which comprises reacting an oxirane represented by the general formula

 (II)

wherein $R^1$ and $R^2$ are as defined above, an amide compound represented by the general formula

$R^3CONHR^4$ (III)

wherein $R^3$ and $R^4$ are as defined above, and carbon monoxide in the presence of hydrogen, a cobalt-containing catalyst and a promoter composed of a compound containing a metal selected from Groups I, II, III and IV of the periodic table.

In the formulae (II) and (III), the alkyl group which may be substituted represented by $R^1$ to $R^4$ may be linear or branched. Suitable alkyl and cycloalkyl groups generally have up to 20 carbon atoms, preferably up to 8 carbon atoms. Examples include methyl, ethyl, propyl, isopropyl, butyl, isobutyl, t-butyl, pentyl, isopentyl, neopentyl, hexyl, isohexyl, heptyl, octyl, nonyl, decyl, undecyl, dodecyl, tridecyl, tetradecyl, pentadecyl, hexadecyl, heptadecyl, octadecyl, nonadecyl, eicosyl, cyclopropyl, cyclopentyl and cyclohexyl.

Substituents which may be present on the alkyl anbd cycloalkyl group include halogen atoms such as bromine, chlorine and fluorine, alkoxy groups such as methoxy, ethoxy, propoxy, isopropoxy, butoxy and benzyloxy, aryloxy groups such as phenoxy, p-methoxyphenoxy, o-chlorophenoxy, and naphthoxy, and aryl groups such as phenyl, tolyl, zylyl, anisyl, and p-dimethylaminophenyl. Specifice examples of the substituted alkyl group are trifluoromethyl, methoxymethyl, ethoxymethyl, methoxyethyl, propoxypropyl, phenoxymethyl, benzyl, chloromethyl, and fluoromethyl.

The term "lower" used herein to qualify a group or compound means that the group or compound has up to 6, preferably up to 4, carbon atoms.

Suitable aryl groups may be substituted are phenyl and napthyl. The heteroaromatic group is furyl, pyrrolyl, pyridinyl, thienyl or indolyl. The phenyl group is preferred. Examples of substituents on the aryl and heteroaromatic group include alkyl groups such as methyl and ethyl, groups such as methoxy, ethoxy, and benzyloxy, a hydroxyl group, halogens such as bromine, chlorine and fluorine, amino substituents such as dimethylamino and acetylamino, and groups such as methylthio, ethylthio, phenylthio and benzylthio. Specific examples of the substituted aryl and heteroaromatic groups are tolyl, xylyl, methoxyphenyl, hydroxyphenyl, dihydroxyphenyl, bromophenyl, chlorophenyl, fluorophenyl, pentafluorophenyl, methylfuryl, N-methypyrrolyl, chloropyridnyl, methylthienyl, N-acetylindolyl, bromonaphthyl, and dimethylaminophenyl.

Illustrative of the oxirane of general formula (II) used as one starting material in the process of this invention are 1-alkylene oxides such as ethylene oxide, propylene oxide, 1-butene oxide, 1-octene oxide, isobutene oxide and dococene oxide; unsubstituted or substituted styrene oxides such as styrene oxide, $\alpha$-methylstyrene oxide, p-hydroxystyrene oxide, p-methoxystyrene oxide, m- or p-dihydroxystyrene oxide, m-bromostyrene oxide, p-trifluoromethylstyrene oxide, o-fluorostyrene oxide, pentafluorostyrene oxide and p-(dimethylamino)styrene oxide; glycidyl ethers such as glycidyl methyl ether, glycidyl chloromethyl ether and glycidylphenyl ether; and heteroaromatic substituted ethylene oxides such as thienyl ethylene oxide, furyl ethylene oxide, N-methylpyrrolyl ethylene oxide, pyridyl ethylene oxide and N-acetylindolyl ethylene oxide. The oxirane may be chosen properly depending upon the kind of the N-acyl-$\alpha$-amino acid to be produced. Styrene oxide, which is a material for N-acyl-$\alpha$-phenylalanines, is most interesting industrially.

Many of the amide compounds of general formula (III) can be easily obtained industrially, and examples include formamide, substituted or unsubstituted aliphatic amides such as acetamide, chloroacetamide, propionamide, lauroylamide, acrylamide, and crotonamide; and substituted or unsubstituted aromatic amides such as benzamide, p-chlorobenzamide, p-methoxybenzamide, m-fluorobenzamide, and p-methylbenzamide.

Carbon monoxide to be reacted with the oxirane of formula (II) and the amide compound of formula (III) need not necessarily be pure, and may be a gaseous mixture containing hydrogen, or may contain another gas which does not substantially affect the reaction, such as nitrogen, carbon dioxide, methane and other gases which are usually involved in commercial synthetic gas.

The characteristic feature of the process of this invention is that the reaction of the oxirane of formula (II), the amide compound of formula (III) and carbon monoxide is carried out in the presence of hydrogen, a cobalt-containing catalyst, and a promoter composed of a compound containing a metal selected from Groups I, II, III and IV of the periodic table.

The cobalt-containing catalyst may be any cobalt-containing catalysts which have heretofore been used as catalyst in a carbonylation or hydroformylation reaction. For example, cobalt-containing compounds are used advantageously. Specific examples of the cobalt-carbonyl compounds include dicobalt octacarbonyl, tetracobalt dodecacarbonyl, hexacobalt hexadecacarbonyl, hydride cobalt tetracarbonyl, sodium cobalt tetracarbonyl, potassium cobalt tetracarbonyl, cobalt tricarbonyl nitrosyl, cyclopentadienyl cobalt dicarbonyl, bistriphenyl phosphine dicobalt hexacarbonyl, and acetylene dicobalt nonacarbonyl.

Such a cobalt-carbonyl compound need not be a previously prepared one. As required, it is possible to form a cobalt-carbonyl compound in situ by adding to the reaction system in accordance with this invention a cobalt compound capable of forming the cobalt-carbonyl compound, such as a cobalt salt of an inorganic or organic acid (e.g., cobalt carbonate or cobalt acetate), and reacting it with carbon monoxide in the reaction system.

Among these, dicobalt octacarbonyl and hydride cobalt tetracarbonyl, especially the former, are preferred because they are available at low cost and their handling in industry has been established.

Examples of the compound containing a metal selected from Groups I, II, III and IV of the periodic table used as the promoter include halides of the metals, such as LiCl, LiBr, $ZnCl_2$, $ZnI_2$, AgF and AgCl; alkoxides of the metals, such as $Ti(OR)_4$, $Al(OR)_3$ and $B(OR)_3$ (wherein R represents an alkyl group such as methyl, ethyl, isopropyl or butyl, or an aromatic group such as a phenyl group, a substituted phenyl group, a naphthyl group, a furyl group, or a thienyl group); hydroxides of the metals, such as $Mg(OH)_2$, $B(OH)_3$ and $Al(OH)_3$; oxides of the metals, such as MgO, CaO, ZnO, $TiO_2$, $SiO_2$, $Al_2O_3$ and $B_2O_3$; acetylacetonates of the metals, such as $Zn(acac)_2$ and $Al(acac)_3$ (wherein acac represents an acetylacetonato group); adn $Mg(ClO_4)_2$. Of these, the titanium and alumninum compounds, especially titanium tetraalkoxides and aluminum trialkoxides, above all titanium tetraisopropoxide and aluminum triisopropoxide, are preferred because they are available at low cost and lead to good yields of the desired products.

The amount of the cobalt-containing catalyst can be varied over a wide range depending, for example, upon its kind. Generally, its amount is conveniently 0.001 to 0.1 mole, preferably 0.005 to 0.05 mole, per mole of the oxirane of formula (II). The amount of the promoter also not strictly limited, and can be varied widely depending upon its kind, the kind of the cobalt-containing catalyst, etc. Generally, it is advantageous to use the promoter in an amount of 0.1 to 10 moles, preferably 0.5 to 4 moles, per mole of the cobalt-containing catalyst.

The amount of the amide compound of formula (III) used in accordance with the process of this invention is not critical. The suitable amount of the amide compound (III) is generally 0.5 to 5 moles, per mole of the oxirane compound.

Carbon monoxide as an additional reactant may be used in an amount such that its partial pressure in the reaction system is 10 to 300 atmospheres. Preferably, the process of this invention is carried out under a carbon monoxide partial pressure of 50 to 150 atmospheres from the viewpoint of economy and safety and because of the need to maintain the catalyst stable and to perform the reaction smoothly.

The presence of hydrogen in the reaction system is for the purpose of increasing the yield of the final product and the rate of the reaction. Usually, hydrogen may be present under a partial pressure of 1 to 100 atmospheres, preferably 20 to 70 atmospheres.

The ratio of carbon monoxide to hydrogen in the reaction system is not critical. Advantageously, the ratio of the partial pressure of carbon monoxide to that of hydrogen is from 0.3 to 10.

Usually, it is preferred to carry out the reaction of this invention in a solvent. Examples of suitable solvents used for this purpose include ethers such as tetrahydrofuran, dioxane, dimethoxyethane and diethyl ether; aromatic hydrocarbons such as benzene, toluene and xylene; esters such as ethyl acetate; ketones such as acetone and diethyl ketone; and aprotic polar solvents such as dimethylformamide.

The reaction temperature can generally be selected from the range of 50° to 300° C., but temperatures of 100° to 200° C. are preferred because at these temperatures, the final desired product is obtained in good yields.

According to the process of this invention described hereinabove, the N-acyl-α-amino acid of formula (I) can be produced in good yields in one step from the oxirane (II) and the amide compound (III) with great industrial advantage. For example, according to the process of this invention, N-acetylphenylalanine can be obtained in a yield of as high as 72 to 98% from styrene oxide and acetamide as will be seen from Examples given hereinafter.

The product of this invention is an aromatic amino acid. It is important not only as an essential amino acid, but also as source substances for hormones, nervous stimulation transmitters, etc. which serve to maintain metabolic balance in a living body. The aromatic amino acid produced by this invention is useful as a food additive, and a material for the production of aspartyl phenylalanine methyl ester which is a low-calorie sweetener. p-bis(2-Chloroethyl)amino-L-phenylalanine is used as an anticancer agent. Phenylalanine is produced in part by a fermentative method, but mostly by synthetic methods. The process of this invention starting from styrene oxide is very useful in industry because of its low cost of production.

The following examples illustrate the present invention more specifically.

EXAMPLE 1

A 200 ml stainless steel autoclave was charged with 6.0 g (50 millimoles) of styrene oxide, 3.0 g (50 millimoles) of acetamide, 300 mg (0.88 millimole) of dicobalt octacarbonyl and 236 mg (0.83 millimole) of titanium tetraisopropoxide as catalysts, and 50 ml of 1,4-dioxane as a solvent, the mixture was stirred at 110° C. for 12 hours under a carbon monoxide pressure of 50 atmospheres and a hydrogen pressure of 50 atmospheres. After cooling, the pressure of the autoclave was returned to normal atmospheric pressure, and the solvent was evaporated under reduced pressure. Then, 100 ml of a 5% aqueous solution of sodium carbonate was added, and the mixture was extracted with ethyl acetate to remove the unreacted acetamide, etc. Phosphoric acid (about 30 ml) was added to the aqueous layer to acidify it to a pH of 1, and it was extracted freshly with ethyl acetate to give 5.25 g (yield 51%) of N-acetylphenylalanine having a melting point of 147° to 150° C. as white crystals. The structure of the product was determined from its NMR and infrared absorption spectra.

EXAMPLE 2

A 200 ml stainless steel autoclave was charged with 3.60 g (30 millimoles) of styrene oxide, 1.77 g (30 millimoles) of acetamide, 341 mg (1.0 millimole) of dicobalt octacarbonyl and 284 mg (1.0 millimole) of titanium tetraisopropoxide as catalyst, and 50 ml of 1,4-dioxane as a solvent, and the mixture was stirred at 110° C. for 12 hours under a carbon monoxide pressure of 50 atmospheres and a hydrogen pressure of 50 atmospheres. After cooling, the pressure of the autoclave was returned to normal atmosphperic pressure, and the resulting solution was worked up in the same way as in Example 1 to give 4.48 g (yield 72%) of N-acetylphenylalanine as white crystals.

EXAMPLE 3

A 50 ml stainless steel autoclave was charged with 2.40 g (20 millimoles) of styrene oxide, 1.18 g (20 millimoles) of acetamide, 227 mg (0.67 millimole) of dicobalt octacarbonyl and 186 mg (0.67 millimole) of titanium tetraisopropoxide as catalysts, and 30 ml of tetrahydrofuran as a solvent, and the mixture was stirred at 110° C. for 16 hours under a carbon monoxide pressure of 80 atmospheres and a hydrogen pressure of 20 atmoshperes. After cooling, the pressure of the autoclave was returned to normal atmospheric pressure, and the solvent was evaporated under reduced pressure. Then, 50 ml of a 5% aqueous solution of sodium carbonate was added, and the mixture was extracted with ethyl acetate to remove the unreacted acetamide, etc. Phosphoric acid (about 15 ml) was added to the aqueous layer to acidify it to a pH of 1. It was extracted freshly with ethyl acetate to give 3.80 g (yield 92%) of N-acetylphenylalanine as white crystals.

EXAMPLE 4

A 100 ml stainless steel autoclave was charged with 3.60 g (30 millimoles) of styrene oxide, 3.63 g (30 millimoles) of benzamide, 341 mg (1.0 millimole) of dicobalt ocatacarbonyl and 284 mg (1.0 millimole) of titanium tetraisopropoxide as catalysts, and 50 ml of tetrahydrofuran as a solvent, and the mixture was stirred at 110° C. for 6 hours under a carbon monoxide pressure of 50 atmospheres and a hydrogen pressure of 50 atmospheres. After cooling, the pressure of the autoclave was returned to normal atmoshperic pressure, and the solvent was evaporated under reduced pressure. Then, 70 ml of a 5% aqueous solution of sodium carbonate was added, and the mixture was extracted with ethyl acetate to remove the unreacted acetamide, etc. Phosphoric acid (about 20 ml) was added to the aqueous layer to acidify it, and then it was extracted freshly with ethyl acetate to give 3.13 g (yield 39%) of N-benzoylphenylalanine having a melting point of 177.5° to 179° C. The structure of the product was determined from its NMR and infrared absorption spectra.

EXAMPLE 5

A 100 ml stainless steel autoclave was charged with 3.60 g (30 millimoles) of styrene oxide, 1.18 g (20 millimoles) of acetamide, 342 mg (1.0 millimole) of dicobalt octacarbonyl and 204 mg (1.0 millimole) of aluminum triisopropoxide as catalysts, and 50 ml of tetrahydrofuran as a solvent, and the mixture was stirred at 110° C. for 17 hours under a carbon monoxide pressure of 50 atmospheres and a hydrogen pressure of 50 atmospheres. After cooling, the pressure of the autoclave was returned to normal atmospheric pressure. The resulting solution was worked up in the same was as in Example 4 to give 3.0 g (yield 72%) of N-acetylphenylalanine as white crystals.

EXAMPLE 6

A 100 ml stainless steel autoclave was charged with 3.60 g (30 millimoles) of styrene oxide, 1.77 g (30 millimoles) of acetamide, 338 mg (0.99 millimole) of dicobalt octacarbonyl and 114 mg (about 1.0 millimole) of hydrous lithium bromide as catalysts, and 50 ml of tetrahydrofuran as a solvent, and the mixture was stirred at 110° C. for 12.5 hours under a carbon monoxide pressure of 50 atmospheres and a hydrogen pressure of 50 atmospheres. After cooling, the pressure of the autoclave was returned to normal atmoshperic pressure. The resulting solution was worked up in the same way as in Example 4 to give 3.27 g (yield 53%) of N-acetylphenylalanine as white crystals.

EXAMPLE 7

A 100 ml autoclave was charged with 3.60 g (30 millimoles) of styrene oxide, 1.77 g (30 millimoles) of acetamide, 341 mg (1.0 millimole) of dicobalt octacarbonyl and 1.0 g (17 millimoles) of silica gel as catalysts, and 50 ml of tetrahydrofuran as a solvent, and the mixture was stirred at 110° C. for 12 hours under a carbon monoxide pressure of 50 atmoshperes and hydrogen pressure of 50 atmospheres. After cooling, the pressure of the autoclave was returned to normal atmospheric pressure. The resulting solution was worked up in the same way as in Example 4 to give 4.46 g (yield 72%) of N-acetylphenylalanine as white crystals.

EXAMPLE 8

A 100 ml autoclave was charged with 2.40 g (20 millimoles) of styrene oxide, 1.17 g (20 millimoles) of acetamide, 227 mg (0.67 millimole) of dicobalt octacarbonyl and 90.9 mg (0.67 millimole) of zinc chloride as catalysts, and 30 ml of tetrahydrofuran as a solvent, and the mixture was stirred at 110° C. for 12 hours under a carbon monoxide pressure of 50 atmoshperes and a hydrogen pressure of 50 atmospheres. After cooling, the pressure of the autoclave was returned to normal atmospheric pressure. The resulting solution was worked up in the same way as in Example 3 to give 2.99 g (yield 72%) of N-acetylphenylalanine as white crystals.

EXAMPLE 9

A 100 ml stainless autoclave was charged with 2.16 g (30 millimoles) of 1-butene oxide, 1.77 g (30 millimoles) of acetamide, 341 mg (1.0 millimole) of dicobalt octacarbonyl and 568 mg (2.0 millimole) of titanium tetraisopropoxide as catalysts, and 50 ml of tetrahydrofuran as a solvent, and the mixture was stirred at 110° C. for 12 hours under a carbon monoxide pressure of 50 atmospheres and a hydrogen pressure of 50 atmoshperes. After cooling, the pressure of the autoclave was returned to normal atmospheric pressure, and the resulting solution was concentrated under reduced pressure. Then 70 ml of a 5% aqueous solution of sodium carbonate was added, and the mixture was extracted with ethyl acetate to remove the unreacted acetamide, etc. Phosphoric acid (about 20 ml) was added to the aqueous layer to acidify it to a pH of 1. It was extracted freshly with ethyl acetate to give a mixture of N-acetylnorvaline as white crystals and by-product β-hydroxy-n-valeric acid as an oil. Chloroform was added to the mixture, and the mixture was filtered to give 1.30 g (yield 27%) of N-acetylnorvaline having a melting point of 109° to 112° C. as white crystals. The structure of the product was determined from its NMR and infrared absorption spectra.

EXAMPLE 10

A 100 ml stainless steel autoclave was charged with 1.74 g (30 millimoles) of propylene oxide, 3.54 g (60 millimoles) of acetamide, 341 mg (1.0 millimole) of dicobalt octacarbonyl and 568 mg (2.0 millimoles) of titanium tetraisopropoxide as catalysts, and 50 ml of tetrehydrofuran as a solvent, and the mixture was stirred at 110° C. for 12 hours under a carbon monoxide pressure of 50 atmospheres and a hydrogen pressure of 50 atmospheres. After cooling, the pressure of the autoclave was returned to normal atmospheric pressure, and the resulting solution was worked up in the same way as in Example 9 to give 0.80 g (yield 18%) of N-acetyl-α-aminobutyric acid having a melting point of 128° to 130° C. as white crystals. The structure of the product was determined from its NMR and infrared absorption spectra.

EXAMPLE 11

A 100 ml stainless steel autoclave was charged with 2.23 g (15 millimoles) of phenylglycidyl ether, 1.77 g (30 millimoles) of acetamide, 171 mg (0.50 millmole) of dicobalt octacarbonyl and 63.5 mg (0.50 millimoles) of silver fluoride as catalysts, and 30 ml of tetrahydrofuran as a solvent, and the mixture was stirred at 110° C. for 13 hours under a carbon monoxide pressure of 50 atmospheres and a hydrogen pressure of 50 atmospheres. After cooling, the pressure of the autoclave was returned to normal atmospheric pressure. The resulting solution was worked up in the same way as in Example 9 to give a mixture of α-acetylamino-γ-phenoxy-n-butyric acid and β-hydroxy-γ-phenoxy-n-butyric acid. Chloroform was added to the mixture, and it was filtered to give 0.60 g (yield 17%) of α-acetylamino-γ-phenoxy-n-butyric acid having a melting point of 144° to 146° C. as white crystals. The structure of the product was determined from its NMR and infrared absorption spectra.

EXAMPLE 12

A 50 ml stainless steel autoclave was charged with 2.26 g (15 millimoles) of phenylglycidyl ether, 1.77 g (30 millimoles) of acetamide, 171 mg (0.50 millimole) of dicobalt octacarbonyl and 63.5 mg (0.50 millimole ) of silver fluoride as catalysts, and 30 ml of 1,4-dioxane as a solvent, and the mixture was stirred at 110° C. for 13 hours under a carbon monoxide pressure of 50 atmospheres and a hydrogen pressure of 50 atmospheres. After cooling, the pressure of the autoclave was returned to normal atmospheric pressure, and the resulting solution was concentrated under reduced pressure. Then, 50 ml of a 5% aqueous solution of sodium carbonate was added, and the mixture was extracted with ethyl acetate to remove the unreacted acetamide, etc. Phosphoric acid (15 ml) was added to the aqueous layer to acidify it, and it was extracted freshly with ethyl acetate to give 0.60 g (yield 17%) of α-acetylamino-γ-phenoxy-n-butyric acid as white crystals.

EXAMPLE 13

A 100 ml stainless steel autoclave was charged with 3.60 g (30 millimoles) of styrene oxide, 1.18 g (20 millimoles) of acetamide, 342 mg (1.0 millimole) of dicobalt ocatcarbonyl and 284 mg (1.0 millimole) of titanium tetraisopropoxide as catalyst, and 60 ml of tetrahydrofuran as a solvent, and the mixture was stirred at 120° C. for 15 hours under a carbon monoxide pressure of 130 atmospheres and a hydrogen pressure of 50 atmospheres. After cooling, the pressure of the autoclave was returned to normal atmoshperic pressure, and the resulting solution was worked up in the same way as in Example 4 to give 3.96 g (yield 95%) of N-acetylphenylalanine as white crystals.

COMPARATIVE EXAMPLE 1

A 200 ml stainless steel autoclave was charged with 6.0 g (50 millimoles) of styrene oxide, 3.0 g (50 millimoles) of acetamide, 300 mg (0.88 millimole) of dicobalt octacarbonyl as a catalyst, and 50 ml of 1,4-dioxane as a solvent, and the mixture was stirred at 140° C. for 2 hours under a carbon monoxide pressure of 150 atmospheres and a hydrogen pressure of 50 atmospheres. After cooling, the pressure of the autoclave was returned to normal atmoshperic pressure, and the solvent was evaporated under reduced pressure. Then, 100 ml of a 5% aqueous solution of sodium carbonate was added, and the mixture was extracted with ethyl acetate to remove the unreacted acetamide, etc. Phosphoric acid (about 30 ml) was added to the aqueous solution to acidify it to a pH of 1, and the mixture was extracted freshly with ethyl acetate to give 2.94 g (yield 28%) of N-acetylphenylalanine having a melting point of 138° to 142° C. The structure of the product was determined from its NMR and infrared absorption spectra.

EXAMPLE 14

A 100 ml stainless steel autoclave was charged with 3.60 g (30 millimoles) of styrene oxide, 1.18 g (20 millimoles) of acetamide, 341 mg (1.0 millimole) of dicobalt ocatcarbonyl and 284 mg (1.0 millimole) of titanium tetraisopropoxide as catalysts, and αml of tetrahydrofuran as a solvent, and they were stirred at 120° C. for 15 hours under a carbon monoxide pressure of 80 atmospheres and a hydrogen pressure of 50 atmospheres. After cooling, the pressure of the autoclave was returned to normal atmoshperic pressure, and the resulting solution was worked up in the same way as in Example 4 to give 4.07 g (yield 98%) of N-acetylphenylalanine as white crystals.

EXAMPLE 15

In a stainless steel autoclave, 9.6 g (80 millimoles) of styrene oxide, 4.7 g (80 millimoles) of acetamide and 120 ml of tetrahydrofuran as a solvent were heated at 120° C. under a carbon monoxide pressure of 100 atmoshperes and a hydrogen pressure of 20 atmospheres. Then, 0.91 g (2.67 millimoles) of dicobalt octacabonyl and 0..76 g (2.68 millimoles) of titanium tetraisopropoxide were added as catalysts, and the mixture was stirred at 120° C. for 2 hours. After cooling, the pressure of the autoclave was returned to normal atmoshperic pressure, and the solvent was evaporated from the resulting solution under reduced pressure. About 100 ml of a 5% aqueous solution of sodium carbonate was added to the residue, and the mixture was extracted with ethyl acetate to remove the unreacted acetamide, etc. About 30 ml of phosphoric acid was added to the aqueous layer to acidify it, and it was extracted with a fresh supply of ethyl acetate to give 14.78 g (yield 89.3%) of N-acetylphenylalanine as white crystals.

What we claim is:

1. A process for producing an N-acyl-α-amino acid of the formula

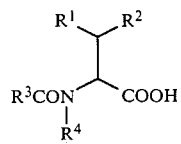

wherein $R^1$, $R^2$, $R^3$ and $R^4$, independently of each other, represent hydrogen; alkyl or cycloalkyl of up to 20 carbon atoms which may be substituted by halogen, benzyloxy, phenoxy, p-methoxyphenoxy, o-chlorophenoxy, naphthoxy, phenyl, tolyl, xylyl, anisyl or p-dimethylaminophenyl; or an aryl or heteroaromatic group which may be substituted by benzyloxy, hydroxyl, halogen, dimethylamino, acetylamino, methylthio, ethylthio, phenylthio of benzylthio, said aryl or hetero-aromatic group being phenyl, naphthyl, furyl, pyrrolyl, pyridinyl, thienyl or indolyl, which comprises reacting an oxirane of the formula

wherein $R^1$ and $R^2$ are as defined above, an amide compound of the formula $$R^3CONHR^4 \qquad (III)$$

wherein $R^3$ and $R^4$ are as defined above, and carbon monoxide in the presence of hydrogen, a cobalt-containing catalyst, and a promoter comprising a compound containing a metal selected from Groups I, II, III and IV of the periodic table.

2. The process of claim 1 wherein the cobalt-containing catalyst is a cobalt-carbonyl compound.

3. The process of claim 1 wherein the cobalt-containing catalyst is dicobalt octacarbonyl.

4. The process of claim 1 wherein the metal is titanium or aluminum.

5. The process of claim 1 wherein the promoter is a titanium tetraalkoxide or an aluminum trialkoxide.

6. The process of claim 5 wherein the promoter is titanium tetraisopropoxide or aluminum triisopropoxide.

7. The process of claim 1 wherein the cobalt-containing catalyst is used in an amount of 0.001 to 0.1 mole per mole of the oxirane.

8. The process of claim 1 wherein the promoter is used in an amount of 0.1 to 10 moles per mole of the cobalt-containing catalyst.

9. The process of claim 1 wherein the reaction is carried out under a carbon monoxide partial pressure of 50 to 150 atmospheres.

10. The process of claim 1 wherein the reaction is carried out under a hydrogen partial pressure of 1 to 100 atmospheres.

11. The process of claim 9 wherein the ratio of the partial pressure of carbon monoxide to the partial pressure of hydrogen is from 0.3 to 10.

12. The process of claim 1 wherein the reaction is carried out at a temperature of 100° to 200° C.

13. The process of claim 1 wherein $R^1$, $R^2$ and $R^3$, independently of each other, represent hydrogen; alkyl or cycloalkyl of up to 8 carbon atoms which may be substituted as defined in claim 1; or phenyl which may be substituted as defined in claim 1; and $R^4$ is hydrogen.

14. The process of claim 10 wherein the ratio of the partial pressure of carbon monoxide to the partial pressure of hydrogen is from 0.3 to 10.

15. A process for producing an N-acetyl-α-amino acid of the formula

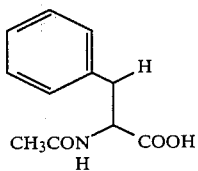

which comprises reacting styrene oxide of the formula

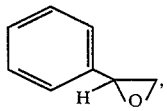

an amide of the formula

CH$_3$CONH$_2$, and carbon monoxide in the presence of hydrogen, a cobalt-containing catalyst, and a promoter comprising a compound containing a metal selected from Groups I, II III and IV of the periodic table.

* * * * *

UNITED STATES PATENT AND TRADEMARK OFFICE
CERTIFICATE OF CORRECTION

PATENT NO. : 4,497,964

DATED : February 5, 1985

INVENTOR(S) : Iwao OJIMA and Kenji HIRAI

It is certified that error appears in the above-identified patent and that said Letters Patent is hereby corrected as shown below:

Column 1, line 19, change "subsituted" to --substituted--;

Column 2, line 60, change "anbd" to --and--;

Column 4, line 36, change "adn" to --and--;

Column 5, line 6, the numeral "10" should be lightfaced;

Column 5, line 38, change "p-bis(2-Chloroethyl)" to --p-bis(2-chloroethyl)--;

Column 6, line 7, change "catalyst" to --catalysts--;

Column 9, line 60, change "0..76" to --0.76--.

Signed and Sealed this

Twenty-third Day of July 1985

[SEAL]

Attest:

DONALD J. QUIGG

Attesting Officer

Acting Commissioner of Patents and Trademarks